US00PP17046P2

(12) United States Plant Patent
Boeder

(10) Patent No.: US PP17,046 P2
(45) Date of Patent: Aug. 22, 2006

(54) ***CHRYSANTHEMUM* PLANT NAMED 'CEREGINA WHITE'**

(50) Latin Name: *Chrysanthemum morifolium*
Varietal Denomination: Ceregina White

(75) Inventor: Mark Roland Boeder, The Hague (NL)

(73) Assignee: Chrysanthemum Breeders Association N.V., Aalsmeer (NL)

( * ) Notice: Subject to any disclaimer, the term of this patent is extended or adjusted under 35 U.S.C. 154(b) by 24 days.

(21) Appl. No.: 11/128,369

(22) Filed: May 13, 2005

(51) Int. Cl.
*A01H 5/00* (2006.01)

(52) U.S. Cl. ..... Plt./288

(58) Field of Classification Search ..... Plt./288
See application file for complete search history.

*Primary Examiner*—Kent Bell
*Assistant Examiner*—Annette H Para
(74) *Attorney, Agent, or Firm*—Steptoe & Johnson LLP

(57) ABSTRACT

A *Chrysanthemum* plant named 'Ceregina White' characterized by its large sized spider type blooms with white ray-florets, with a response time of 52 days, and which is grown as a disbud.

3 Drawing Sheets

BACKGROUND OF THE INVENTION

'Ceregina White' is a product of a breeding-program which had the objective of creating new *chrysanthemum* cultivars with a double type flower, a 7.5 week response and a medium plant height (90 cm). The new plant of the present invention comprises a new and distinct cultivar of *Chrysanthemum* plant. 'Ceregina White' is a seedling from a cross in a breeding program maintained under the control of inventor. The female parent is #92154-unpatented-, an unnamed seedling not available to inventor for description. The male parent is unknown, being a mixed population of a group of male parents. The new and distinct cultivar was discovered and selected as a flowering plant within the progeny of the stated cross by Mark Roland Boeder in a controlled environment (greenhouse) in Rijsenhout, The Netherlands in 2001. The first act of asexual reproduction of 'Ceregina White' was accomplished when vegetative cuttings were taken from the initial selection in 2001 and propagated further in a controlled environment in Rijsenhout, The Netherlands.

SUMMARY OF THE INVENTION

The present invention is a new and distinct variety of *chrysanthemum* bearing large sized double type blooms with white ray-florets, which is grown as a disbud.

BRIEF DESCRIPTION OF THE DRAWINGS

The present invention of a new and distinct variety of *chrysanthemum* is shown in the accompanying drawings, the color being as nearly true as possible with color photographs of this type.

DESCRIPTION OF THE INVENTION

Figure 1:
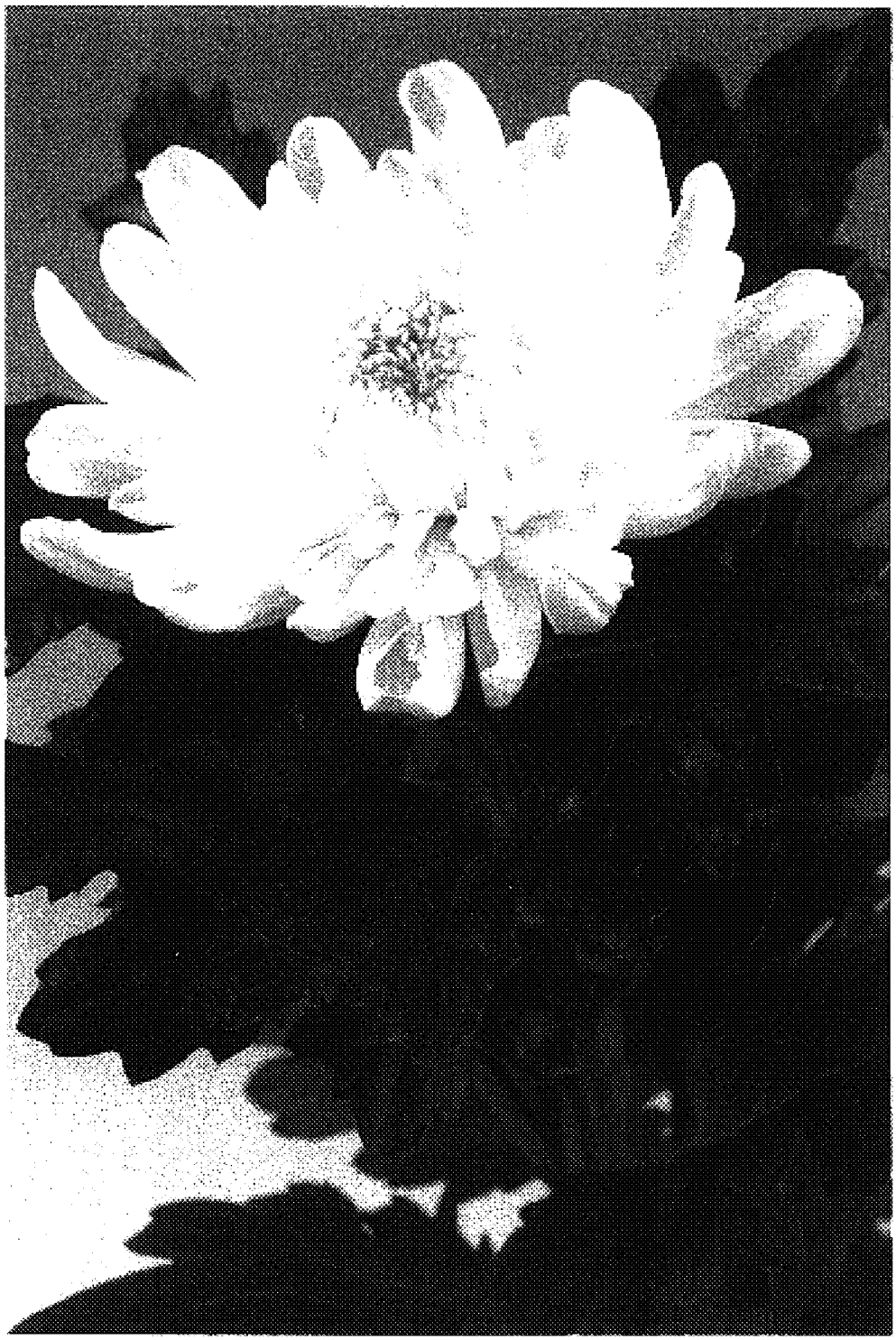
FIG. 1 shows a plant of the cultivar in full bloom.
Figure 2:
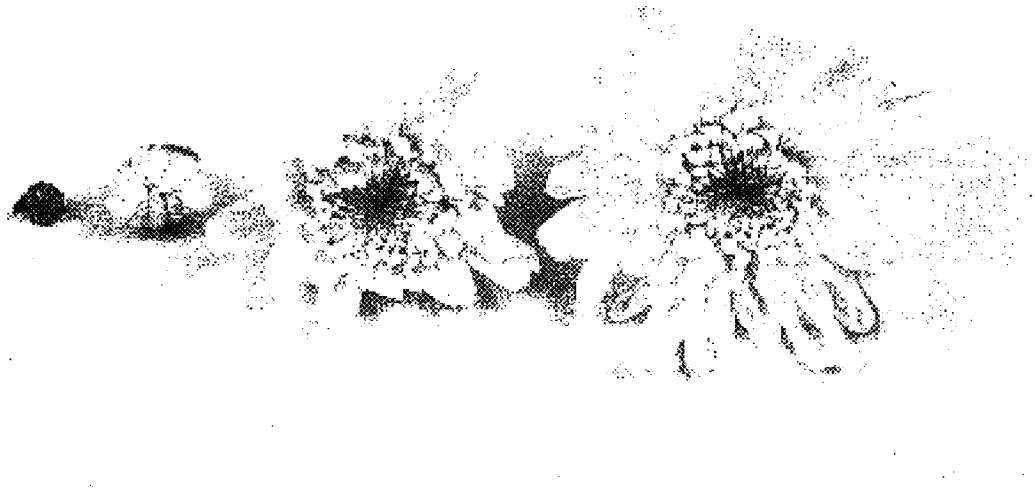
FIG. 2 shows the various stages of bloom of the new cultivar.
Figure 3:
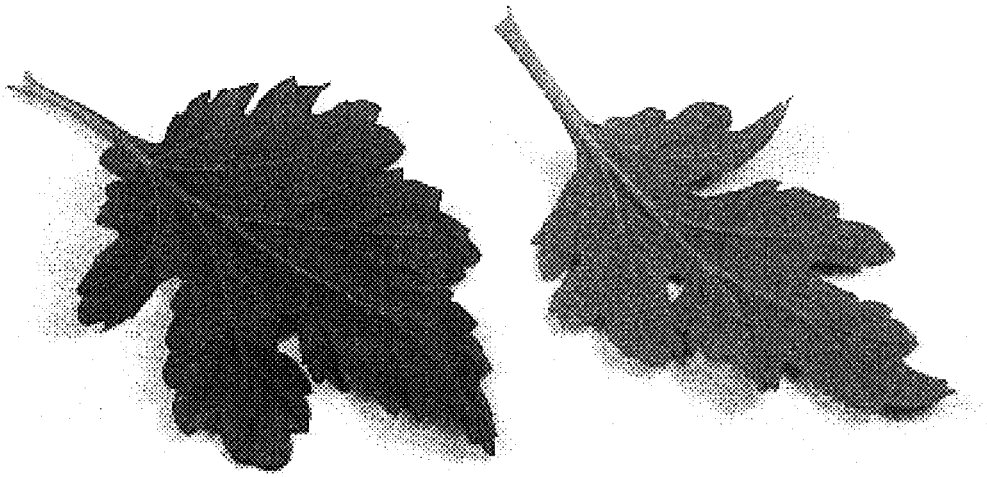
FIG. 3 shows the foliage of the new cultivar.

This new variety of *chrysanthemum* is of the botanical classification *Chrysanthemum morifolium*. The observations and measurements were gathered from plants grown in April/May in a greenhouse in Rijsenhout, The Netherlands in a photo-periodic controlled crop under conditions generally used in commercial practice. The greenhouse temperatures during this crop were at day-time between 18° C. and 25° C. and at night 20° C. After a long day period of 14 days the photo-periodic response time in this crop was 52 days. After the long day period to flowering growth retardants were applied 2 to 3 times in an average dose of 2.5 gram/liter water. The plants were observed (directly) during the flowering of this crop. No tests were done on disease or insect resistance or susceptibility. No tests were done on cold or drought tolerance. This new variety produces large sized blooms with white ray-florets blooming on the plant for 1 week. This new variety of *chrysanthemum* has been found to retain its distinctive characteristics throughout successive propagations however the phenotype may vary significantly with variations in environment such as light intensity and temperature. To show the phenotype as described 'Ceregina White' can be planted without assimilation lightning (high pressure sodium lamps) between week 4 and week 36 under greenhouse conditions in The Netherlands. With assimilation light (minimum level 2500 lux) it can be planted year round under greenhouse conditions in The Netherlands.

From the cultivars known to inventor the most similar existing cultivar in comparison to 'Ceregina White' is 'Resomee White' (U.S. Plant patent application Ser. No. 11/020,211). When 'Resomee White' and 'Ceregina White' are being compared the following differences and similarities are noticed: Both 'Resomee White' and 'Ceregina White' have white double type blooms. The differences of 'Resomee White' and 'Ceregina White' are (1) Center of the bloom. In the mature stage, the center of the bloom is cream in 'Resomee White' and yellow-green in 'Ceregina White'. (2) Cross section of ray florets. The cross section is flat to concave in 'Resomee White' and convex in'Ceregina White'. (3) Longitudinal axis of majority of ray florets. This axis is straight in 'Resomee White' and incurving in 'Ceregina White'.

The following is a description of the plant and characteristics that distinguish 'Ceregina White' as a new and distinct variety. The color designations are taken from the plant itself. Accordingly, any discrepancies between the color designations and the colors depicted in the photographs are due to photographic tolerances. The color chart used in this description is: The Royal Horticultural Society Colour Chart, edition 1995.

TABLE 1

Botanical Description of variety '*Ceregina White*'

| | |
|---|---|
| Bud | |
| Size | Large, cross-section 1 cm height 1 cm |
| Outside color | Yellow-green 145D |
| Phyllaries | 2 rows, length 7 mm, width 3 mm |
| Involucral bracts among disc-florets | Not present |
| Involucral bracts color | Green 138B |
| Inflorescence | |
| Type | Double |
| Height | 2 cm |
| Size | large |
| Fully expanded | 11–12 cm |
| Number of blooms per stem | 1 (disbud) |
| Performance on the plant | 1 week |
| Seeds (if crossed) | Seed production not observed |
| Fragrance | Typical *chrysanthemum*, slight |
| Peduncle length | 2 cm |
| Peduncle color | Green 136C |
| Color | |
| Center of the flower | Immature Yellow-green 149D<br>Mature Yellow-green 154D |
| Color of the ray-florets | Upper surface White 155D<br>Lower surface White 155D |
| Tonality from Distance | A disbud mum with white double type flowers |
| Color of the upper surface of the ray-florets after aging of the plant | White 155D |
| Ray florets | |
| Texture | Upper and under side smooth |
| Number | 220–230 |
| Cross section | Convex |
| Longitudinal axis of majority | Incurving |
| Length of corolla tube | 0.4 cm |
| Ray-floret margin | Entire |
| Ray-floret length | 4.5–5 cm |
| Ray-floret width | 0.8–1.4 cm |
| Ratio length/width | High |
| Shape of tip | Round |
| Disc florets | |
| Disc diameter | 0.5 cm |
| Distribution of disc florets | Few, only visible in mature stage of flowering |
| Shape | Tubular |
| Color | Yellow 11D |
| Receptacle shape | Conical raised |
| Reproductive Organs | |
| Stamen | Present in disc florets only |
| Stamen color | Yellow-green 144 A |
| Pollen | Produced in small amount |

TABLE 1-continued

Botanical Description of variety '*Ceregina White*'

| | |
|---|---|
| Pollen color | Yellow 7A |
| Styles | Present in both ray and disc florets |
| Style color | Yellow 13A |
| Style length | 3 mm |
| Stigma color | Yellow-green 145 D |
| Stigma Width | 1 mm |
| Ovaries | Enclosed in perianth |
| Plant | |
| Form | A disbud mum meant for erect culture |
| Growth habit | Upright |
| Growth rate | Moderate |
| Height | 90 cm |
| Width | 25 cm |
| Internode length | 2–2.5 cm |
| Stem Color | Green 136 C with ribs of Green 138C |
| Stem Strength | Strong |
| Stem Brittleness | Brittle |
| Stem Anthocyanin coloration | Absent |
| Flowering Response (photo-periodic controlled crop, not natural season) | 52 days (summer) to 55 days (winter) |
| Foliage | |
| Color immature stage | Upper side Green 141A<br>Under side Green 138B |
| Color mature stage | Upper side Green 137 B–C<br>Under side Green 138 A–B |
| Color midvein mature leaf | Upper side Yellow-green 147D<br>Under side Yellow-green 147D |
| Size | Large; length 15–16 cm, width 8–8.5 cm |
| Quantity (number per single stem) | 30 |
| Shape | Ovate |
| Texture upper side | Fleshy and glabrous |
| Texture under side | Pubescent |
| Venation arrangement | Palmate |
| Shape of the margin | Serrated |
| Shape of Base of Sinus Between Lateral Lobes | Round |
| Margin of Sinus Between Lateral Lobes | Diverging to parallel |
| Shape of Base | Truncate |
| Apex | Mucronulate |
| Petiole Length | 3.5 cm |
| Petiole Color | Yellow-green 147D |

TABLE 2

Differences with comparison variety

| | '*Ceregina White*' | '*Resomee White*' |
|---|---|---|
| Center mature bloom | Yellow-green 154D | Yellow-white 158D |
| Cross section ray florets | Convex | Flat to concave |
| Longitudinal axis of majority of ray florets | Incurving | Straight |

I claim:

1. A new and distinct variety of *chrysanthemum* plant as described and illustrated.

* * * * *